(12) United States Patent
Frisch et al.

(10) Patent No.: US 6,904,308 B2
(45) Date of Patent: Jun. 7, 2005

(54) ARRAY SYSTEM AND METHOD FOR LOCATING AN IN VIVO SIGNAL SOURCE

(75) Inventors: Mordechai Frisch, Moreshet (IL); Arkady Glukhovsky, Nesher (IL); Daphna Levy, Carmiel (IL)

(73) Assignee: Given Imaging Ltd., Yoqncam (IL)

( * ) Notice: Subject to any disclaimer, the term of this patent is extended or adjusted under 35 U.S.C. 154(b) by 242 days.

(21) Appl. No.: 10/150,018

(22) Filed: May 20, 2002

(65) Prior Publication Data

US 2002/0173718 A1 Nov. 21, 2002

(30) Foreign Application Priority Data

May 20, 2001 (IL) .................................................. 14326

(51) Int. Cl.[7] .............................................. A61B 5/05
(52) U.S. Cl. ........................................ 600/424; 606/2
(58) Field of Search ................................ 600/424, 419, 600/407, 410, 411, 425; 606/2, 20, 27, 32; 324/307, 308, 309

(56) References Cited

U.S. PATENT DOCUMENTS

| | | | |
|---|---|---|---|
| 4,219,821 A | * | 8/1980 | Selim .......................... 342/445 |
| 4,278,077 A | | 7/1981 | Mizumoto |
| 4,329,881 A | | 5/1982 | Schloss |
| 5,042,486 A | | 8/1991 | Pfeiler et al. |
| 5,211,165 A | | 5/1993 | Dumoulin et al. |
| 5,279,607 A | | 1/1994 | Schentag et al. |
| 5,429,132 A | | 7/1995 | Guy et al. |
| 5,515,853 A | | 5/1996 | Smith et al. |
| 5,592,180 A | * | 1/1997 | Yokev et al. ................ 342/450 |
| 5,604,531 A | | 2/1997 | Iddan et al. |
| 5,697,377 A | | 12/1997 | Wittkampf |
| 5,736,958 A | * | 4/1998 | Turpin ......................... 342/179 |
| 5,913,820 A | | 6/1999 | Bladen et al. |
| 6,172,640 B1 | | 1/2001 | Durst et al. |
| 6,188,355 B1 | | 2/2001 | Gilboa |
| 6,190,395 B1 | | 2/2001 | Williams |
| 6,233,476 B1 | | 5/2001 | Strommer et al. |
| 6,453,190 B1 | * | 9/2002 | Acker et al. ................. 600/424 |
| 6,580,938 B1 | * | 6/2003 | Acker ......................... 600/424 |
| 6,690,963 B2 | * | 2/2004 | Ben-Haim et al. .......... 600/424 |
| 2003/0167000 A1 | | 9/2003 | Mullick et al. |

FOREIGN PATENT DOCUMENTS

| | | |
|---|---|---|
| EP | 0 667 115 | 8/1995 |
| JP | 6154191 | 6/1994 |
| JP | 6285044 | 10/1994 |
| JP | 111985 | 5/1995 |
| JP | 711985 | 5/1995 |
| JP | 7255692 | 10/1995 |
| JP | 2001046358 | 2/2001 |
| JP | 2001231186 | 8/2001 |
| JP | 2001231187 | 8/2001 |
| WO | WO 98/11816 | 3/1998 |
| WO | WO 99/32028 | 7/1999 |
| WO | WO 00/10456 | 3/2000 |
| WO | WO 01/06917 | 2/2001 |
| WO | WO 01/08548 | 2/2001 |
| WO | WO 03/021529 | 3/2003 |
| WO | WO 03/028224 | 4/2003 |
| WO | PCT/IL03/00834 | 10/2003 |

OTHER PUBLICATIONS

U.S. Appl. No. 10/200,548, filed Jul. 23, 2002, Glukhovsky et al.

(Continued)

*Primary Examiner*—Daniel Robinson
(74) *Attorney, Agent, or Firm*—Pearl, Cohen, Zedek, Latzer, LLP

(57) ABSTRACT

A system and method for localizing an in vivo signal source using a wearable antenna array having at least two antenna elements. The signal is received and a signal strength is measured at two or more antenna elements. An estimated coordinate set is derived from the signal strength measurements.

23 Claims, 5 Drawing Sheets

OTHER PUBLICATIONS

Park, et al., *"Design of Bi–directional and Multi–Channel Miniaturized Telemetry Module for Wireless Endoscopy"*, $2^{nd}$ Annual International IEEE–EMBS Special Topic Conference on Microtechnologies in Medicine &Biology, May 2–4, 2002, Madison, Wisconsin USA pp. 273–276.

Park, et al., *"Design of Miniaturized Telemetry Module for Bi–Directional Wireless Endoscopy"*, May 2–4, 2002.

Park, et al., *"A Technique for Localization of Biomedical Telemetry Sensor in Human Body"*, Proceedings of the International Sensor Conference 2001, Seoul, Korea.

Nam, et al., *"A method for Position Detection of the wireless capsule endoscopes Module Using the Solution of Nonlinear Simultaneous Equations"*, Sensors Conference 2002, p. 377.

Nam, et al., *"A method for Position Detection of Miniaturized Telemetry Module Using the Solution of Nonlinear Simultaneous Equations"*, 2002.

*"Localization of a wireless capsule endoscope in the GI Tract"*, Gastrointestinal Endoscopy 2001;53:AB126.

* cited by examiner

ARRAY SYSTEM AND METHOD FOR LOCATING AN IN VIVO SIGNAL SOURCE

FIELD OF THE INVENTION

The present invention relates generally to an in vivo camera system and in particular to a system and method for identifying the position of such an in vivo camera system.

BACKGROUND OF THE INVENTION

Various in vivo measurement systems are known in the art. They typically include ingestible electronic capsules which collect data and which transmit the data to a receiver system. These capsules, which are moved through the digestive system by peristalsis, include "Heidelberg" capsules to measure pH, "CoreTemp" capsules to measure temperature and other capsules to measure pressure throughout the intestines. They have also been used to measure gastric residence time and intestinal passage time, which is the time it takes for food to pass through the stomach and intestines.

The intestinal capsules typically include a measuring system and a transmission system, where the transmission system transmits the measured data at radio frequencies to the receiver system. Alternate systems can store all the data within a storage device in the capsule. The data can then be read after the capsule exits the gastrointestinal (GI) tract.

In vivo camera systems are known, such one known camera system which is carried by a swallowable capsule. The in vivo video camera system captures and transmits images of the GI tract while the capsule passes through the gastrointestinal lumen. The system includes a capsule that can pass through the entire digestive tract and operate as an autonomous video endoscope.

Prior attempts at localizing an intra-gastric and intrauterine transmitting capsule includes spatially scanning a non-ambulatory patient with a receiver. The receiver and scanning system locates the points with the highest reception and plots a track of the capsule, the assumption being that the capsule is at the location where the strongest signal is received. These attempts use a laboratory device that is non-portable and non-commercial.

Other attempts at localizing an in vivo capsule analyze the statistics of signal variation during the passage of the capsule through the GI tract. Large signal level variations are observable during the passage of the capsule through specific significant locations in the lumen and these variations are associated with specific anatomical features. This method is inherently inaccurate since the anatomically significant locations of the GI tract are not rigidly attached to a fixed frame of reference.

SUMMARY OF THE INVENTION

As part of the present invention, there is an antenna array having multiple antenna elements. The antenna array may be fixed to a body, and two or more antenna element may receive a signal from an in vivo signal source. A signal strength of a received signal may be measured and an estimated location of the signal source may be derived from the signal strength measurements.

BRIEF DESCRIPTION OF THE DRAWINGS

The subject matter regarded as the invention is particularly pointed out and distinctly claimed in the concluding portion of the specification. The invention, however, both as to organization and method of operation, together with containers, features, and advantages thereof, may best be understood by reference to the following detailed description when read with the accompanying drawings in which:

Figure 1B:
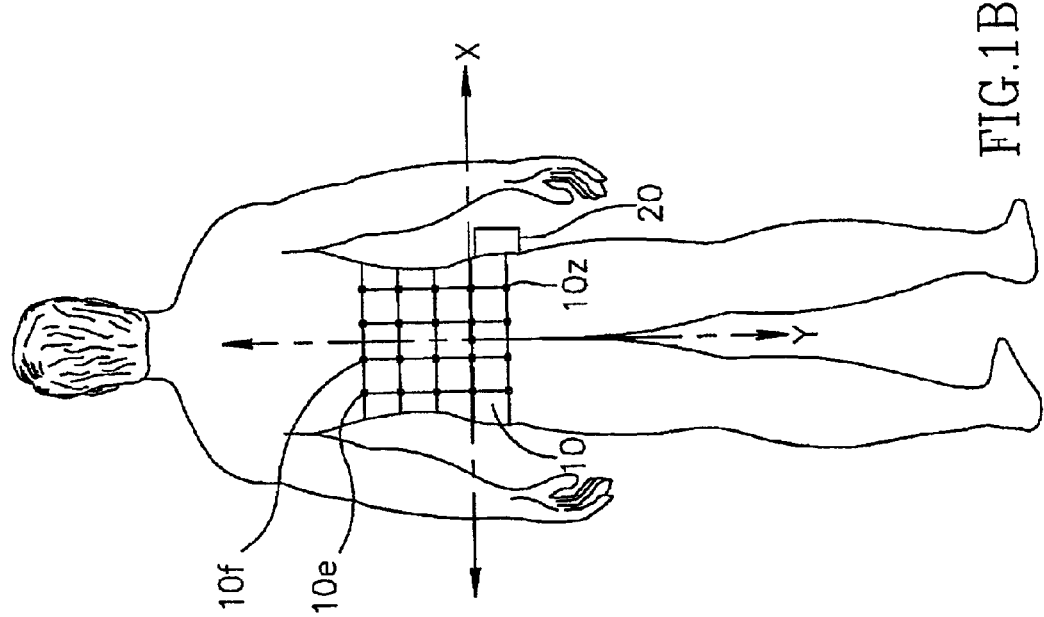
FIGS. 1A and 1B show a person wearing an antenna array according to an embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

Unless specifically stated otherwise, as apparent from the following discussions, it is appreciated that throughout the specification discussions utilizing terms such as "processing", "computing", "calculating", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

Figure 1A:
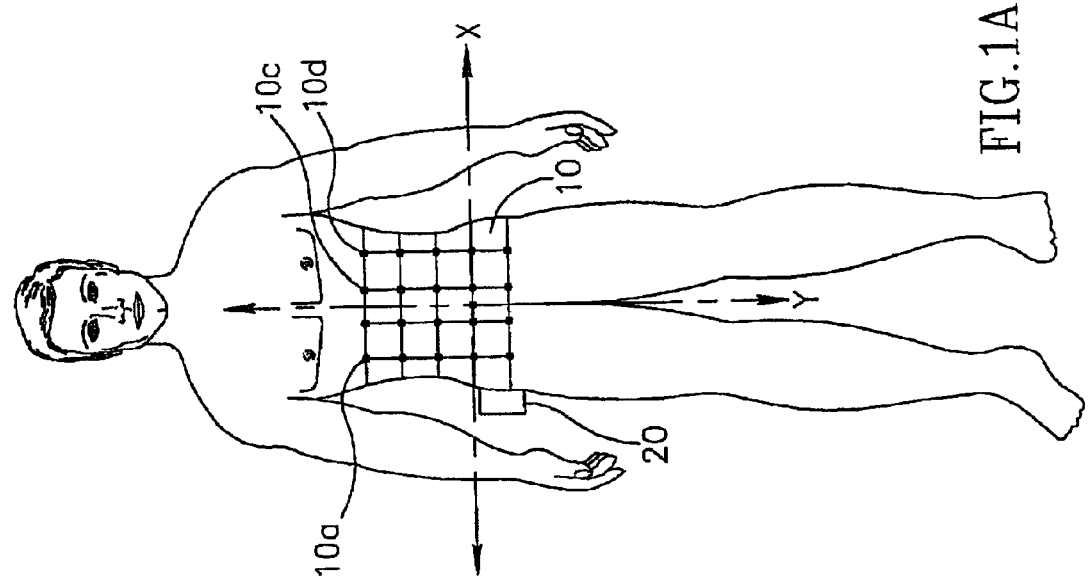

Reference is now made to FIGS. 1A and 1B. As part of the present invention, an in vivo signal source may be localized using a wearable antenna array or antenna array belt 10, as shown in FIGS. 1A and 1B. The antenna array belt 10 is fitted such that it may be wrapped around a patient and attached to a signal recorder 20. Additional embodiments include antenna elements having adhesive, which may adhere the element to a point on a body. Each of the antennas elements 10a through 10z in the array may connect via coaxial cables to a connector, which connects to the recorder 20. Each antenna element 10a through 10z may be a loop antenna, or may be any other antenna configuration known in the art.

In one embodiment the antenna array belt includes eight antenna elements that are typically positioned on a subject's midsection. For example, the antenna elements can be positioned as follows. A first antenna element is positioned on the intersection of the right $7^{th}$ intercostal space and right mid clavicular line; a second antenna element is positioned on the xiphoid process; a third antenna element is positioned on the intersection of the left $7^{th}$ intercostal space and left mid clavicular line; a fourth antenna element is positioned on the right lumbar region at umbilical level; a fifth antenna element is positioned above the naval; a sixth antenna element is positioned on the left lumbar region at umbilical level; a seventh antenna element is positioned on the right mid-linguinal region; and an eighth antenna element is positioned on the left mid-linguinal region. Other antenna positions and other numbers of antennas may be used. For example, an antenna array may be positioned on a subjects back.

Figure 2:
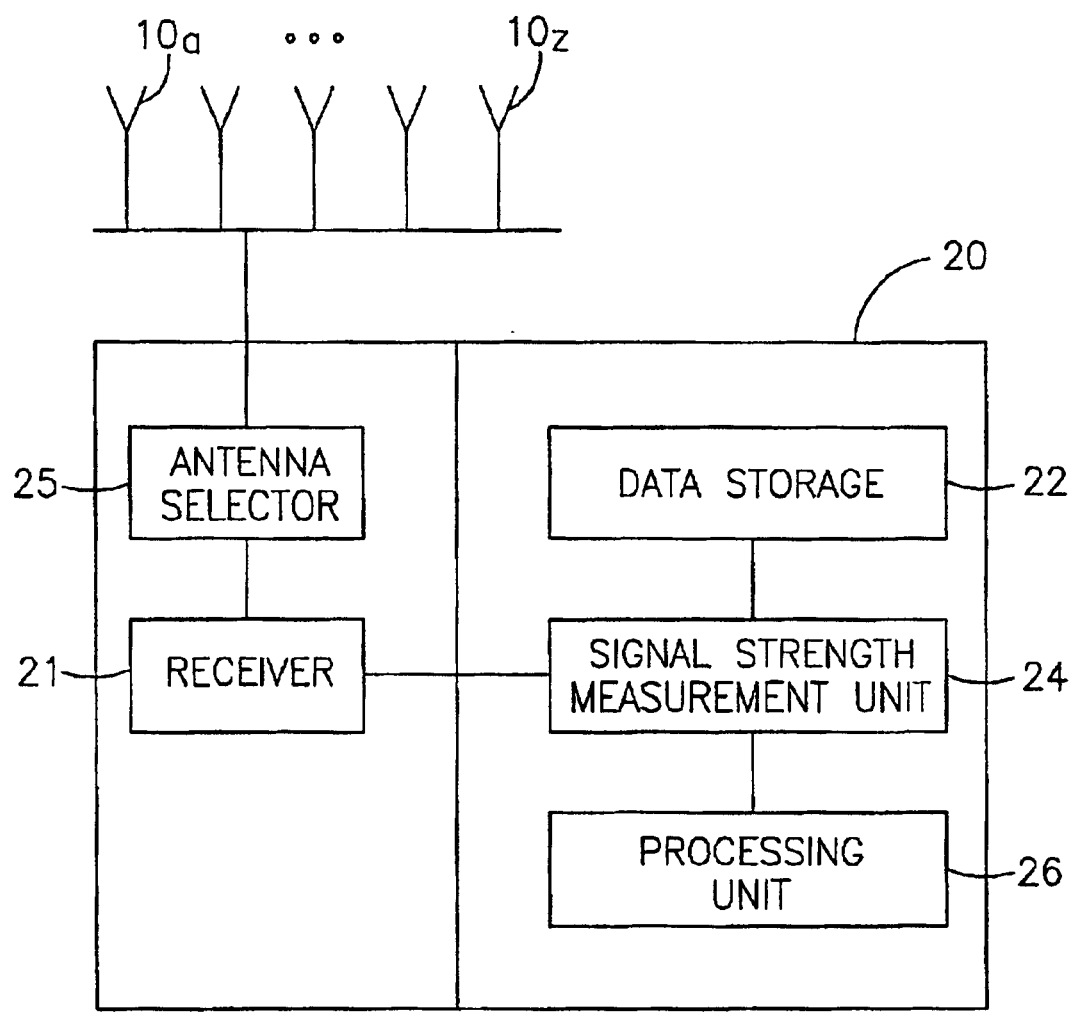
FIG. 2. shows a data recorder according to an embodiment of the present invention.

Aside from having a data storage unit 22, the data recorder 20 may also have a receiver 21, a signal strength measurement unit 24, a processing unit 26, and an antenna selector 25 as shown in FIG. 2. In alternate embodiments the data recorder 20 may include other combinations of components, and the components described may be divided among other units. The signal strength measurement unit 24 may measure the signal strength of signals received by the receiver 21 from each of the antenna elements 10a through 10z, and the processing unit 26 may perform calculations to correlate the received signal with an estimated location of the source of the signal. The antenna selector 25 may open a signal path to single antenna element from which the receiver 21 will receive a signal. The antenna selector 25 may be adjusted to scan through all or subset of antenna elements 10a through 10z. The scan rate and pattern may be adjusted to maximize signal to noise ratios for the received signals.

Figure 3:
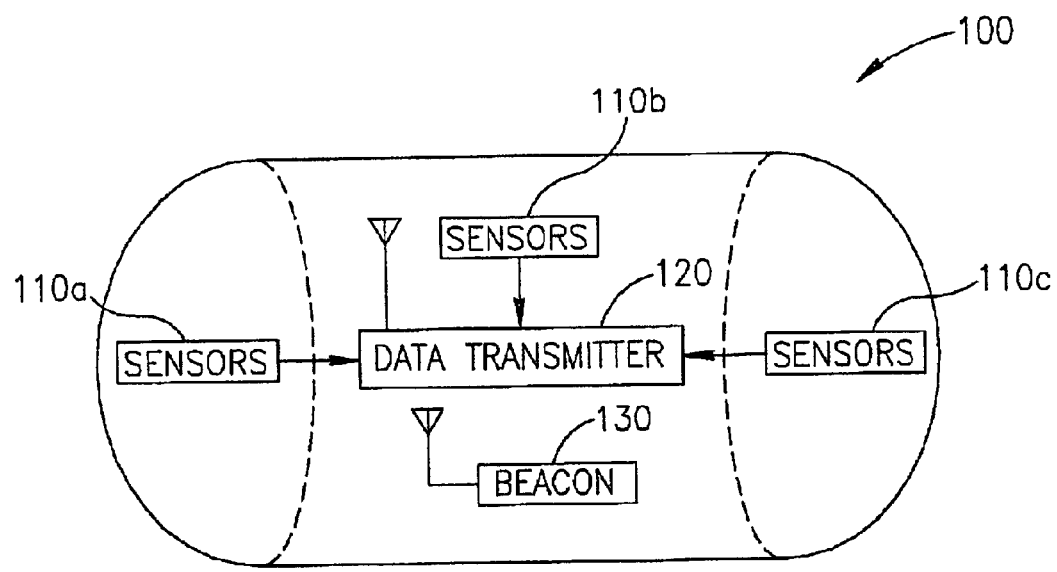
FIG. 3. shows an in vivo signal source according to an embodiment of the present invention.

Turning now to FIG. 3, there is shown an example of an in vivo signal source 100 according to one embodiment of the present invention. The source 100 is a capsule, which may be ingested. The capsule 100 may contain several sensors such as temperature 110a, PH 110b, and optical 110c. Other sensors or sets of sensors may be used. The sensors 110 may provide data, for example, to a data transmitter 120. A beacon 130 may send out an intermittent beacon signal, or the beacon 130 may be instructed to transmit at or about the same time the data transmitter 120 transmits a data signal. Typically, the data transmitter 120 will transmit at a higher frequency than the beacon 130, but need not. In one embodiment of the present invention the data transmitter 120 may transmit a non-modulated signal as a beacon signal. In one embodiment the capsule is similar to or may comprise components similar to embodiments described in the art.

Figure 4:
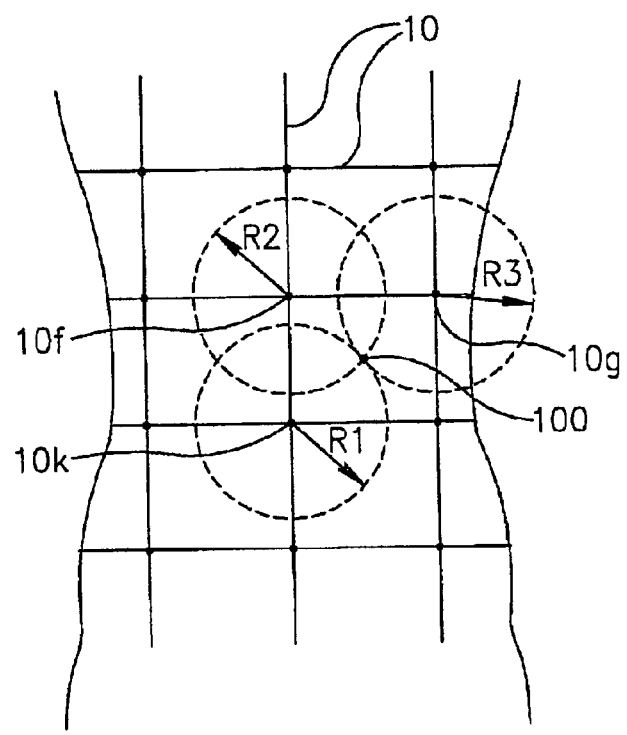
FIG. 4. shows a torso wearing an antenna array according to an embodiment of the present invention and an estimated point of a signal source.

Turing now to FIG. 4, there is shown a close-up of a human torso wearing a belt 10 or adhesive antenna array according to an embodiment of the present invention. Also visible is an estimated location of an in vivo signal source 100. The location is shown as the intersection point of three circles having radius R1, R2 and R3. Each radius value being an estimated distance value of the source 100 from each of antenna elements 10k, 10f and 10g, receptively. The distance values may be calculated by the processing unit 26 based on signal strength measurements preformed by signal strength measurement unit 24. For example, the propagation assumption used in processing the localization signal data assumes that radiation attenuation is linear within the body. This is equivalent to $$I_r = I_o \propto \alpha^* r, \qquad \text{(Eq. 1)}$$

where r is the distance (in cm) between the capsule and the antenna, $I_o$ is the signal level (in dBm) at the capsule, $I_r$ is the signal level (in dBm) at r, and $\alpha$ is the absorption coefficient (in dB/cm). The assumption of linear attenuation is valid at the working frequency range (200–500 MHz) and at intermediate distances between the transmitter and receiver, i.e. for distances of half a wavelength to 2–2.5 wavelengths. Knowing the signal level at the source and the measured signal level at each antenna, one can derive the distance between the source and the antenna.

General signal source triangulation techniques as shown in FIG. 4 are well known. For purposed of completeness, however, the following is yet another example of a method of estimating the location of an in vivo signal source according to the present invention.

Figure 5:
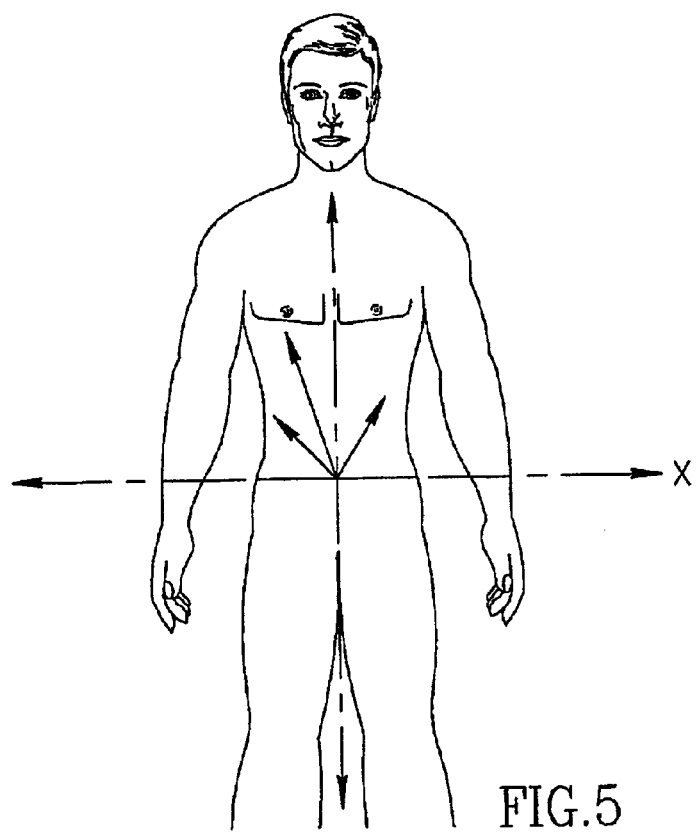
FIG. 5. shows a three signal vectors in a two dimensional plane.

Shown in FIG. 5 are three signal vectors relating to signals received at three antenna elements 10d, 10p, 10q. Beginning at the origin of a coordinate system centered at the naval, each signal vector points in the direction of its respective antenna element and has a magnitude relating to the strength of the received signal. Each signal vector may be calculated as the product of a pointing vector from the origin to the point where its respective antenna element is placed, multiplied by a normalized received signal value. A normalized signal strength value may be computed by dividing each measured signal strength value by the strongest measured value. This results in the strongest measured value being normalized to 1, and the rest to values smaller than one. Thus, the signal vector pointing to an antenna element receiving the strongest signal level will look identical to its pointing vector. The other signal vectors will be shorter than their pointing vectors.

Figure 6:
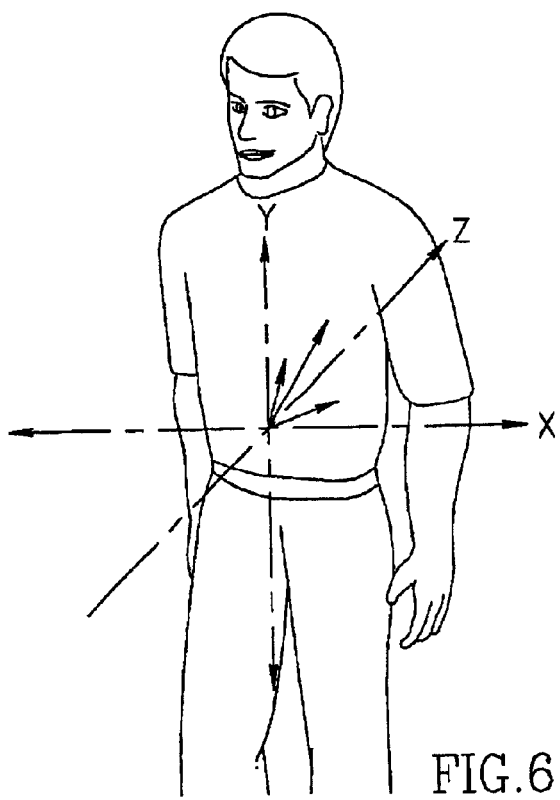
FIG. 6. shows a three signal vectors in three dimensional space.

The estimated point or location of the signal source 100 may be estimated as the vector sum of all the signal strength vectors, the location vector. Signal vectors may be calculated for two or more antenna elements 10a through 10z. Signal vectors can be calculated for only elements placed at the front of the torso, or as FIG. 6 shows, signal vectors may also be calculated for elements placed at the back of the body (FIG. 1B). The point estimated to be the location of the signal source 100 in FIG. 6 is within the body. Typically, the location vector starts at the origin of a three dimensional system and ends at a point within the body.

As part of the present invention, one may use an absolute coordinate set where points on the body are measured in terms of standard units such as centimeters or inches. Alternatively, one can assign values relative to anatomical points on the body and later normalize the results. For example, an antenna element placed at the naval may be given the coordinate set 0,0; an element placed at the right end of the torso at naval level may be given the coordinate set 5,0; and an element place at left end of the torso −5,0. Distance values or vector magnitudes can be calculated using these coordinate sets. And later the values may be proportionally adjusted to fit the body's actual dimensions. For example, if there was calculated a distance value of 2.5 inches based on the above stated coordinates, but it was later measured that the body was actually 7 unit from naval to the right end, the distance value of 2.5 could be adjusted in the same proportion, 7/5.

Only the two or three strongest signal sources may be used, rejecting the weaker signal strength values, to calculate signal vectors or distance values upon which a location estimate is based. Once the strongest group of signals is identified, a second signal strength measurement may be performed. The processing unit may be adapted to perform a conventional vector sum operation on a subset of the largest vectors, and to perform a weighted sum operation on the signal vectors which are relatively smaller. Other manipulations of the collected signals may be used, using other operations.

The antenna selector 25 may be adjusted to perform a scan of only the antenna elements from which the strongest signals were received, excluding all other antennas. Excluding or rejecting signal information from antennas providing weak signals generally increases signal to noise ratios.

Figure 7:
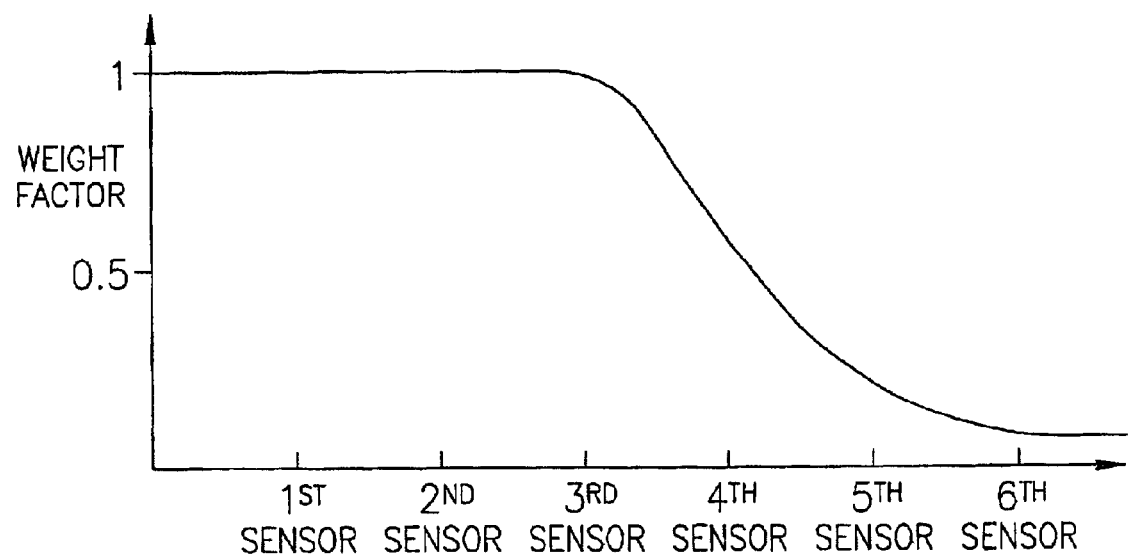
FIG. 7. shows a graph of a weighing function for signal vectors.

However, in another embodiment, location vectors or distance values may be calculated relating to many antenna elements and signal vectors having relatively low magnitudes may be multiplied by a reducing/weighing factor as shown in FIG. 7.

An estimated location of an in vivo signal source may be continuously or semi-continuously tracked. An instantaneous velocity vector for the signal source may be computed using the position information. For example, the velocity vector would be the vector starting at the tip of a first location vector and ending at the tip of a consecutive location vector. Or, the signal source's speed may be computed as a derivative of its position, and its direction may be plotted on a display or a graph functionally associated with the data recorder 20.

In an embodiment of the invention a supplementary procedure for detecting defective antenna elements may be carried out. If an antenna element is determined to be defective the entire trajectory may be invalidated. In an example of such a procedure readings for all frames (if not discarded) are collected, for each antenna, into two bins, for example, Bin1=number of readings in the range 0 to 40 and Bin2=number of readings in the range 41 to 255 or Bin1= number of readings in the range 0 to 107 and Bin2=number of readings in the range 108 to 255. The result is 8 histograms of 2 bins each, one for each antenna. If Bin1/(Bin1+ Bin2)>0.75 the antenna is defective. Else the antenna is OK. The trajectory is considered valid if all antennas are OK. Further, if thReception(n)<60 (for the first example) or if thReception(n)<117 (for the second example) the current sensor readings can be discarded.

While certain features of the invention have been illustrated and described herein, many modifications, substitutions, changes, and equivalents will now occur to those skilled in the art. It is, therefore, to be understood that the appended claims are intended to cover all such modifications and changes as fall within the true spirit of the invention.

What is claimed:

1. A system for localizing an in vivo signal source comprising:
   an antenna array adapted to attach to a body, said array comprising a plurality of antenna elements;
   a signal strength detector connected to said antenna array and adapted to measure at two or more of said antenna elements the signal strength of signals generated from an in-vivo signal source; and
   a processing unit adapted to communicate with said signal strength detector and to correlate the signal strength measurements at two or more of said antenna elements to an approximate coordinate set for the in vivo signal source.

2. The system according to claim 1, further comprising an antenna selector.

3. The system according to claim 2, wherein each of a subset of said plurality of antenna elements is located near a point having a known coordinate set within a coordinate system centered in proximity of the body.

4. The system according to claim 3, wherein said processing unit is adapted to calculate a distance value associated with each signal strength measurement.

5. The system according to claim 4, wherein the process is adapted to estimate the location of the signal source based on the distance values.

6. The system according to claim 3, wherein said processing unit is adapted to calculate a signal vector for each received signal.

7. The system according to claim 6, wherein said processing unit is adapted to perform a vector sum of the calculated vectors.

8. The system according to claim 7, wherein said processing unit is adapted to perform a conventional vector sum operation on a subset of the calculated vectors, the subset being composed of the largest vectors, and to perform a weighted sum operation on the signal vectors which are relatively smaller than the vectors in the subset.

9. The system according to claim 8, further comprising a display unit adapted to display the approximate coordinate set of the signal source.

10. The system according to claim 9, wherein the display unit is adapted to display a representation of a body and a pointer showing the approximate coordinate set of the signal source.

11. The system according to claim 1 wherein the antenna array comprises eight antenna elements.

12. A method for localizing an in viva signal source with a wearable antenna array, said method comprising the steps of:
    receiving a signal generated from the in-vivo signal source at two or more antenna elements within the array;
    measuring the received signal strength; and
    correlating the signal strength measurements to an approximate coordinate set.

13. The method according to claim 12, wherein each of at least two antenna elements is located near a point having a known coordinate set within a coordinate system centered in proximity of the body.

14. The method according to claim 13, further comprising the step of calculating a distance value associated with a received signal.

15. The method according to claim 14, further comprising the step of correlating the location of the signal source using the distance values associated with two or more antenna elements.

16. The method according to claim 13, further comprising the step of calculating a signal vector relating to each received signal.

17. The method according to claim 16, further comprising the step of performing a vector sum operation of the signal vectors.

18. The method according to claim 17, further comprising the step of applying a weighing factor to a signal vector.

19. The method according to claim 18, wherein the weighing factor is applied to signal vectors having a relatively small magnitude.

20. The method according to claim 19, further comprising the step of displaying the signal source's estimated location.

21. The method according to claim 20, wherein the signal sources estimated location is displayed graphically as a pointer with a figure of a body.

22. The method according to claim 12 further comprising the step of localizing the signal source by receiving a signal at two or more antenna elements within the array.

23. A method for localization comprising:

receiving a signal generated from an in viva signal source at two or more antenna elements;

measuring the received signal;

correlating the signal measurements to an approximate coordinate set; and localizing the signal source.

* * * * *